United States Patent [19]
Picciola et al.

[11] Patent Number: 4,902,799
[45] Date of Patent: Feb. 20, 1990

[54] BICYCLIC ALKOXY- AND ALKYLTHIO-SUBSTITUTED AMINOALCOHOLS

[75] Inventors: Giampaolo Picciola, Milan; Mario Riva, Monza; Franco Ravenna, Milan; Piergiorgio Gentili, Bergamo, all of Italy

[73] Assignee: Maggioni-Winthrop S.p.A., Milan, Italy

[21] Appl. No.: 60,393
[22] PCT Filed: Oct. 18, 1986
[86] PCT No.: PCT/EP86/00595
§ 371 Date: Jun. 4, 1987
§ 102(e) Date: Jun. 4, 1987
[87] PCT Pub. No.: WO87/02666
PCT Pub. Date: May 7, 1987

[30] Foreign Application Priority Data

Oct. 14, 1985 [GB] United Kingdom ............... 8525256
Jun. 25, 1986 [GB] United Kingdom ............... 8615562

[51] Int. Cl.$^4$ ............................................. C07D 401/06
[52] U.S. Cl. ..................................... 546/199; 544/365; 544/379; 546/18; 546/206; 564/341; 564/349
[58] Field of Search ............... 546/199, 206; 564/341, 564/349

[56] References Cited

U.S. PATENT DOCUMENTS 4,246,268  1/1981  Carr ................................. 546/206
4,338,323  7/1982  Regnier et al. ................... 546/199
4,552,965  11/1985  Parsons ........................... 546/206

FOREIGN PATENT DOCUMENTS 0076530  4/1983  European Pat. Off. .
0092391  10/1983  European Pat. Off. .

OTHER PUBLICATIONS

Chemical Abstracts, vol. 103, No. 15, Oct. 14, 1985, (Columbus, Ohio, U.S.), see p. 698, abstract 123196w, & JP, A. 60100542, (Otsuka Pharmaceutical Factory, Inc.), Jun. 1985.

Primary Examiner—Glennon H. Hollrah
Assistant Examiner—James H. Turnipseed
Attorney, Agent, or Firm—Oblon, Spivak, McClelland, Maier & Neudstadt

[57] ABSTRACT

Novel bicyclic alkoxy- and alkylthio-substituted aminoalcohols of formula (I). The compounds show antihypertensive, platelet aggregation inhibiting, hypolipemic, antianoxic, spasmolytic, antithrombotic, calcium antagonizing and neuroleptic activity.

6 Claims, No Drawings

BICYCLIC ALKOXY- AND ALKYLTHIO-SUBSTITUTED AMINOALCOHOLS

This invention is concerned with new pharmacologically active compounds. More particularly, the compounds with which this invention is concerned are bicyclic alkoxy- and alkylthio-substituted amino alcohols of the formula:

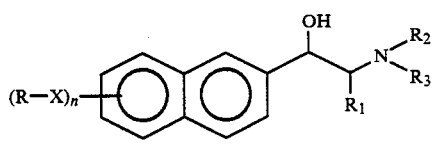
I wherein R represents a lower straight or branched alkyl group, X represents —O— or —S—, n is an integer from 1 to 3, $R_1$ represents hydrogen or a lower alkyl group; $R_2$ represents hydrogen or benzyl; $R_3$ represents an alkyl group; or alternatively $R_2$ and $R_3$ taken together represents a divalent group selected from:

(a)

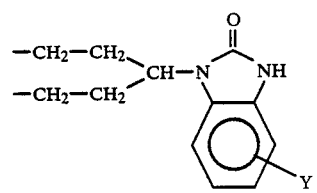

wherein Y represents hydrogen or halogen;

(b)

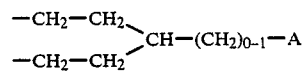

wherein A is a group selected from

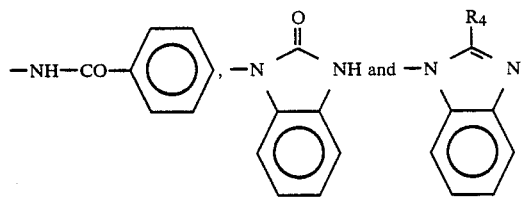

wherein $R_4$ represents a lower alkyl group;

(c)

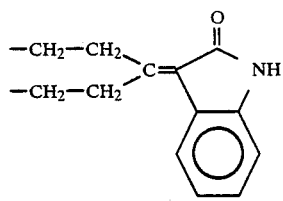

and (d)

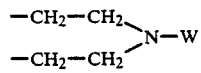

wherein W represents hydrogen, phenyl, benzyl, alkoxyphenyl, methylphenyl, 2-furoyl, nicotinoyl or a radical

in which Z represents 2-thienyl or phenyl optionally substituted with 1-3 halogen, lower alkyl or alkoxy groups: and their salts with inorganic acids, organic acids, cationic exchange resins and complexes with cyclodextrins.

As apparent to all those skilled in organic chemistry, the compounds in which $R_1$ does not represent hydrogen, having two structural asymmetry centers, may exist both in the erythro and threo configuration.

In most cases, by the manufacturing process which will be hereinafter described, a mixture of the two steric isomers is obtained, and an appropriate separation may occasionally be necessary. In other instances, however, formation of one single isomer is so prevailing as to approach 100 per cent, and a separation is not required unless the product is desired in an analytically pure condition for purposes of study.

The configuration of the erythro and threo isomers was assigned through $^1$H.NMR (Nuclear Magnetic Resonance) spectra by determining the characteristic coupling constants ($J_{C-1,C-2}$) of the compounds.

The chemical process for the preparation of the invention compounds consists in contacting a bromo ketone of the partial formula II with an amine to give the amino ketone of the partial formula III.

The amino ketone is then hydrogenated to give the desired amino alcohol

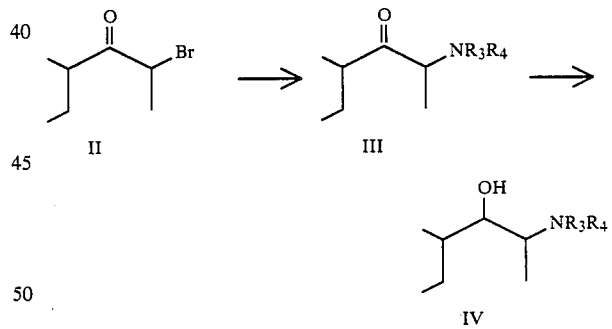

Depending on the circumstances, the amino ketone III may be isolated from the reaction mixture before it is hydrogenated. On the other hand, if the intermediate III shows a low degree of stability, it is preferable to hydrogenate it directly in the reaction mixture in which it is formed by reaction of the bromo ketone with the amine.

The first step of the process is carried out in the presence of a proton acceptor, such as an alkali metal or earth alkali carbonate or bicarbonate or a tertiary amine.

In some instances, an excess over the molecular amount of the same amine which if being contacted with the bromo ketone may be used with satisfactory results. Usually this first step is carried out in a solvent inert to the instant reaction such as a lower alkanol, for instance methanol or ethanol, or a ketone, such as a di-lower alkyl ketone, for instance acetone or methyl ethyl ketone. It is immaterial whether the amine is added to the bromo ketone, both or only one of them being dissolved in the solvent, or vice versa the bromo ketone is added to the amine, still both in solution or only one of them.

The appropriate way of conducting the first step will be selected considering the properties of the reactants and their reactivity. The reaction temperature is also adjusted depending on the reactivity of the two reactants, although normally the boiling temperature of the solvent is generally preferred. The second step of the process, i.e. the hydrogenation, may be carried out by any conventional hydrogenation procedures apt to convert a ketone into an alcohol. However, we have found that the hydrogenation is best performed by using a metal hydride, preferably a double hydride, such as $NaBH_4$, $LiAlH_4$ etc., by conventional procedures in a solvent inert to the hydrogenation reaction, which in the case of $NaBH_4$ may be water, or a lower alkanol, such as methanol or ethanol, both in the presence of various amounts of water of under anhydrous conditions, or alternatively, when for instance $LiAlH_4$ is used, the solvent may be diethyl ether, tetrahydrofuran and the like, at a temperature which may range from $0°-5°$ C. to the boiling temperature of the selected solvent. When the intermediate is not isolated from the reaction mixture of the first reaction step, and depending on the nature of the selected hydrogenating agent, this is added directly to the intermediate reaction mixture either in the form of a solution in an appropriate solvent not interfering with the hydrogenation and the solution of the hydrogenating agent is added while maintaining the mixture at the reflux temperature or at a lower temperature which may be found more convenient depending on the observed reaction rate; or the hydrogenating agent may be added at portions or be dropping its solution in an appropriate solvent while maintaining the reaction mixture at a temperature ranging from $0°$ C. to the boiling temperature of the solution until the addition is complete, then heating the mixture to reflux until the reaction is complete. Obviously the skilled chemist will select the procedure appropriate to the nature of the hydrogenating agent and the substrate and the reactant used.

An alternative process for preparing the invention compounds consists in reacting an amino alcohol of the partial formula V with an aldehyde in a solvent, preferably in a lower alkanol such as methanol or ethanol, at a temperature between about $0°$ C. and

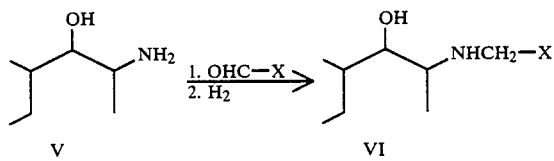

the reflux temperature of the solution.

To the reaction mixture a hydrogenating agent is then added at portions, the agent being preferably selected from metal hydrides or double cyano hydrides, such as sodium cyano boro hydride or lithium cyano boro hydride, these latter hydrogenating agents being preferred.

It is apparent to those having knowledge or organic chemistry that the last described method of preparation is convenient when the symbol X in the partial formula VI above represents a linear or branched alkyl radical.

The compounds of this invention show anti-hypertensive, platelet aggregation inhibiting, hypolipemic, antianoxic, spasmolytic, antithrombotic and $Ca^{++}$ antagonizing activity. These activities are shared both by the individual stereoisomeric forms and their mixtures, which therefore may be administered for therapeutical purposes, depending on the actuale convenience, in one or the other steric form or mixture.

The anti-hypertensive activity was tested on groups of 5 SH rats (spontaneously hypertensive rats) weighing $200\pm10$ g, fasting for 18 hrs and treated orally with the invention compounds suspended in 2.5% gum arabic.

Changes in blood pressure (mm Hg) before ($T=0$) and after treatment (2, 4 and 6 hrs) were measured according to the method of tail artery plethysmography reported in "Spontaneously hypertensive rats (SHR): Guidlines for breeding, care and use", SHR Conference, 1976, page 11.

The heart rate was also tested (BP Recorder No. 8006 supplied by Basile, Comerio, Italy). The arterial pressure before the treatment was $210\pm10$ mmHg.

Table 1 shows that the compounds are endowed with good anti-hypertensive activity at all tested doses.

The peak effect was noted 2-4 hrs after the treatment and the duration of the effect was more than 6 hrs: in this period no remarkable increase of heart rate was registered.

Administration of 5 mg/kg p.o. caused a pressure decrease higher than Tibalosine. At 1 mg/kg p.o. MG 38065 was more effective than Urapidil.

TABLE 1

| COMPOUND | Max. changes in systolic pressure (mmHg) SHR | | |
|---|---|---|---|
| | 15 | 5 | 1 mg/kg p.o. |
| MG 38065 | −41 | −43 | −34.2 |
| MG 38095 | −47.6 | −26.5 | −18 |
| MG 38069 | −68 | −39 | −13.6 |
| MG 14233 | −48.2 | −31 | −14.4 |
| Tibalosine | −67 | −13.2 | ~0 |
| Urapidil | −72.4 | −47 | −16 |

To test the antagonism against phenylephrine (PHE) induced hypertension, male rats CrI:CD (SD)BR were anesthisized with urethane, 1 g/kg i.p.

PHE was administered cumulatively and dose-response curves were obtained (controls). Dose-response curves were similarly obtained after administration of the test drugs (1 mg/kg i.v.). From the two curves the PHE dosis causing a 50 mm Hg increase of the arterial pressure was calculated. The PHE dosis was about 9 times, in comparison with the controls, after administration of MG 38069; 20-25 times after MG 14238, MG 14233 and MG 38065; 34 times after MG 38095.

The protection against toxic adrenaline doses was tested as follows. Groups of 10-20 male mice CrI:CD 1(CR) BR were treated orally with vehicle (controls) and with various doses of the compounds. After 2 hrs 14.5 mg/kg of 1-adrenaline was administered intraperitoneally and mortality was recorded after 24 hrs: in controls mortality was 100%. From log dose-% protection curves the 50% protective doses ($PD_{50}$) were calculated (Litchfield et al., J. Pharmacol. Exp. Ther. 96, 99, 1949).

Table 2 gives the results obtained with some of the compounds as compared with known drugs having alpha-adrenergic receptor blocking activity.

The new compounds show generally the same or higher activity as compared with Tibalosine and Phentolamine; MG 14167 and MG 14233 were comparable with Prazosin.

TABLE 2

| COMPOUND | $PD_{50}$ mg/kg/p.o. | Confidence limits (P = 0.05) |
|---|---|---|
| MG 14167 | 0.6 | 0.50–0.72 |
| MG 38065 | 1.0 | 0.74–1.34 |
| MG 38069 | 5.4 | 3.68–7.92 |
| MG 38088 | 13.5 | 9.23–19.75 |
| MG 14233 | 0.95 | 0.69–1.31 |
| MG 38095 | 3.75 | 2.23–6.30 |
| MG 14235 | 5.05 | 3.44–7.41 |
| MG 14237 | 10.0 | 7.28–13.74 |
| MG 14238 | 1.8 | 1.32–2.60 |
| MG 14239 | 5.8 | 3.59–7.54 |
| Prazosin | 0.70 | 0.59–0.83 |
| Tibalosine | 5.5 | 3.36–8.99 |
| Phentolamine | 8.0 | 6.3–10.15 |

The receptors binding assay for the inhibition of $^3$H-Prazosin, $^3$H-Clonidine and $^3$H-Spiperone binding to rat brain membrane was carried out according to Greenberg et al., Life Sci. 19, 69, 1976 and U'Prichard et al., Molec. Pharmacol. 13, 454, 1977.

Data for the tested compounds are reported in Table 3 where the 50% inhibiting concentrations ($IC_5$) of Tibalosine and Urapidil are also given. The invention compounds show a good affinity toward alpha$_1$-adrenergic receptors, comparable with or higher than the two comparison substances, and poor or no affinity toward alpha$_2$-adrenergic receptors.

A moderate affinity toward serotoninergic$_2$ (5-HT$_2$) receptors is displayed by MG 38069.

Platelet aggregation was stimulated with collagen (2-4 mcg/ml) added simultaneously to PRP of control and treated rats. The results were assessed photometrically. Each test was replicated 4 times in groups of 3 animals. Aggregation curves were evaluated in terms of two parameters namely maximum optical density variation (maximum aggregation) and aggregation rate.

Table 4 gives the effects recorded after treatment with some of the tested compounds. They show an activity comparable to Ticlopidine and Suloctidil and only slightly lower than Sulfinpyrazone.

TABLE 4

| | % Inhibition | |
|---|---|---|
| COMPOUND | Maximum aggregation | Aggregation rate |
| MG 38078 | 70.4 | 64.0 |
| MG 38068 | 58.8 | 54.4 |
| MG 38088 | 68.6 | 75.1 |
| MG 28472 | 75.7 | 65.3 |
| MG 14239 | 64.0 | 64.6 |
| Ticlopidine | 70.0 | 56.0 |
| Sulfinpyrazone | 92.5 | 89.0 |
| Suloctidil | 69.0 | 57.5 |

To test the hypolipemic activity, Sprague Dawley Nos male rats (180–200 g) were treated orally for 4 consecutive days with vehicle (0.5 ml/100 g gum arabic 2.5%, controls) and with 1–3 doses of the tested compounds, and were sacrificed at the 5th day after 18 hrs fasting. Total cholesterol (CHOL), triglycerides (TG), HDL cholesterol (CHOL-HDL) were assayed in serum and the liver was weighed.

Table 5 gives the obtained results. MG 28451, MG 38065, MG 38068 and MG 28453 cause a significative decrease of serum TG and an increase of CHOL-HDL, and the other compounds are effective in decreasing both CHOL and serum TG. Among these, MG 38127 and MG 38105 exert a good activity at very low doses.

TABLE 3

| Compound | Concentration (M) | % Inhibition of specific binding | | |
|---|---|---|---|---|
| | | $^3$H—Prazosin ($\alpha_1$) | $^3$H—Clonidine ($\alpha_2$) | $^3$H—Spiperone [5-HT$_2$] |
| MG 38065 | 5.4 × 10$^{-7}$ | 98 | 0 | 0 |
| | 5.4 × 10$^{-6}$ | 100 | 0 | 38.9 |
| MG 38069 | 5.4 × 10$^{-7}$ | 97 | 0 | 36 |
| | 5.4 × 10$^{-6}$ | 100 | 13 | 83 |
| MG 38095 | 5.4 × 10$^{-7}$ | 98 | 0 | 32 |
| | 5.4 × 10$^{-6}$ | 100 | 12.5 | 62 |
| MG 14167 | 5.4 × 10$^{-7}$ | 99 | 8 | 0 |
| | 5.4 × 10$^{-6}$ | 99 | 26.5 | 25 |
| Tibalosine | $IC_{50}$ (a) | 4 × 10$^{-7}$ | 1 × 10$^{-3}$ | |
| Urapidil | $IC_{50}$ (b) | 8 × 10$^{-7}$ | 1.4 × 10$^{-5}$ | |

(a) QIAN J. H. et al.-Arch. int. Pharmacodyn 266, 264; 1983
(b) VAN ZWIETEN P. A. et al.-Arch. int. Pharmacodyn. 276, 180; 1985

The effect on platelet aggregation was tested ex vivo according to the method of Minsker (J. Pharmacol. Exp. Ther. 210, 37, 1979) slightly modified. Groups of 3 rats (280–350 g) were treated orally with vehicle (controls) and compounds (0.15 mM/kg). Blood was collected and pooled from rats of each group 1 hr after treatment and the platelet rich plasma (PRP) was separated by centrifugation.

The activity of the foregoing compounds is higher than with Clofibrate which, as known, causes a significative liver increase. The Probucol activity is moderate and is noted only after prolonged treatment (8 days).

Finally, in the test of ethanol induced hypertriglyceridemia (Sirtori et al., Atherosclerosis 30, 45, 1978) the decrease of serum TG was significative and higher than 50% after administration of all mentioned compounds at doses of 0.37–0.046 mM/kg per os).

TABLE 5

| COMPOUND | Dose mM/kg/p.o. | Normolipemic rats % different from control | | | |
|---|---|---|---|---|---|
| | | CHOL | TG | CHOL-HDL | Liver Weight |
| MG 28451 | 0.37 × 4 days | −13.5 | −48.2 | +46.5 | +9.2 |

TABLE 5-continued

| COMPOUND | Dose mM/kg/p.o. | Normolipemic rats % different from control | | | |
|---|---|---|---|---|---|
| | | CHOL | TG | CHOL-HDL | Liver Weight |
| MG 38065 | 0.185 × 4 days | +7.2 | −35.6 | +11.8 | −3.6 |
| MG 38065 | 0.37 × 4 days | −18.1 | −49.9 | +42.6 | −0.9 |
| MG 38068 | 0.185 × 4 days | −3.7 | −45.0 | +5.0 | +2.6 |
| MG 38068 | 0.37 × 4 days | −21.8 | −56.9 | +32.9 | +0.3 |
| MG 38088 | 0.185 × 4 days | −35.1 | −70.5 | −9.1 | 0 |
| MG 38088 | 0.37 × 4 days | −41.3 | −68.5 | +5.4 | +3.4 |
| MG 28453 | 0.185 × 4 days | +8.5 | −36.4 | +45.2 | +2.8 |
| MG 28453 | 0.37 × 4 days | −26.9 | −75.4 | +31.7 | +21.6 |
| MG 38127 | 0.023 × 4 days | −30.2 | −41.4 | +7.6 | −1.6 |
| MG 38127 | 0.046 × 4 days | −51.2 | −66.3 | −1.8 | +8.6 |
| MG 38127 | 0.185 × 4 days | −59.1 | −81.7 | −19.8 | +3.3 |
| MG 38105 | 0.023 × 4 days | −35.7 | −36.2 | −13.3 | +5.5 |
| MG 38105 | 0.046 × 4 days | −45.8 | −63.8 | +1.3 | +8.0 |
| MG 38105 | 0.185 × 4 days | −96.6 | −70.6 | +3.9 | +4.8 |
| MG 14244 | 0.37 × 4 days | −42.7 | −54.4 | +38.2 | +8.3 |
| Clofibrate | 0.82 × 4 days | −15.0 | −40.0 | 0 | +19.5 |
| Probucol | 0.205 × 8 days | −25.0 | −28.0 | −26 | +4.0 |
| Probucol | 0.82 × 4 days | ~0 | ~0 | +18.5 | ~0 |

The anti-hypoxic activity was determined according to Yasuda et al., Arch. Int. Pharmacodyn. 233, 136, 1978.

Groups of 10 male mice (21–23 g) were treated orally with vehicle (controls) and the invention compounds. After 45 or 90 minutes the animals were decapitated and the gasping time was determined. Table 6 gives the results obtained after administration of some of the invention compounds which display an activity higher than Suloctidil.

The invention compounds also showed a very low acute toxicity per os in male mice. Thus for instance, the $LD_{50}$ was higher than 1000 mg/kg for MG 14233, MG 28451, MG 38068, MG 38088 and MG 38095, and higher than 2000 mg/kg for MG 14167, MG 14237, MG 14244, MG 38065, MG 38069 and MG 38078.

TABLE 6

| COMPOUND | Dose mg/kg/p.o. | Pretreatment Time (min.) | Gasping time % diff. from control |
|---|---|---|---|
| MG 38077 | 100 | 90 | +71.0 |
| MG 38071 | 100 | 90 | +32.7 |
| MG 38088 | 100 | 45 | +46.8 |
| MG 38088 | 100 | 90 | +32.2 |
| MG 38098 | 100 | 90 | +41.1 |
| MG 14233 | 50 | 90 | +52.5 |
| MG 14233 | 100 | 90 | +126.2 |
| MG 14238 | 50 | 90 | +39.3 |
| MG 14238 | 100 | 90 | +85.7 |
| MG 14239 | 100 | 90 | +61.3 |
| Flunarizine | 50 | 90 | +68.7 |
| Suloctidil | 100 | 45 | +27.5 |
| | 100 | 90 | +11.7 |

It is understood also that what we claim is not limited to the compounds of formula I, but also to the intermediate ketones of formula III, inasmuch they share the valuable pharmacological properties illustrated hereinbefore.

EXAMPLE 1 erythro-2-Octylamino-1-(6-methoxy-2-naphtyl)-propanol (MG 38064)

A mixture of 4 g of 2-bromo-1-(6-methoxy-2-naphthyl)-1-propanone (13.6 mmole) (A. Marquet et al., Bull. Soc. Chim. France 90, 1962), 2.1 g of distilled n-octylamine (16.3 mmole) and 60 ml of methanol is refluxed with stirring for 6 hours. After cooling to room temperature, 1.03 g of $NaBH_4$ (27.2 mmole) are gradually added and stirring is continued for 3 hours at room temperature. The precipitate is collected, washed with water and dried.

The filtered mother liquor was cooled on ice, 18 per cent hydrochloric acid is added to precipitate additional product as the hydrochloride which is collected, recrystallized from methanol/water and converted into the free base, which is combined with the first crop.

On recristallization from methanol/water, 2.7 g of the title compound are obtained. Yield 57%; m.p. 106°–108° C.

| Analysis for $C_{22}H_{33}NO_2\%$ | calc. | C 76.92 | H 9.68 | N 4.08 |
|---|---|---|---|---|
| | found | 76.77 | 9.66 | 4.07 |

The NMR spectrum (CDCl$_3$) gave J=4.0 Hz

EXAMPLE 2 threo-2-(N-Benzyl-N-octylamino)-1-(6-methoxy-2-naphthyl)-propanol (MG 38073)

A mixture of 11.7 g of 2-bromo-1-(6-methoxy-2-naphthyl)-1-propanone (39.9 mmole), 8 g of N-benzyl-N-octylamine (36.5 mmole) (R. E. Lutz et al, J. Org. Chem. 12, 760, 1947), 3.37 g of $NaHCO_3$ (40 mmole) and 150 ml of methanol is refluxed with stirring for 6 hours.

After this time heating to reflux is continued while 2.7 of $NaBH_4$ (72 mmole) dissolved in 15 ml of alkaline water is gradually added.

Stirring is continued overnight at room temperature, then aqueous 18% HCl is added to acidic reaction and the solution is evaporated to dryness under reduced pressure. The residue is treated with methylene dichloride, a 5% aqueous solution of $Na_2CO_3$ is added to neutral reaction and the organic layer is dried and evaporated to dryness in vacuo. The residue is chromatographed through silica gel 60 Merck 70–230 mesh with petroleum ether: ethyl acetate 95:5 as the eluent. Yield 10.5 g (50%).

EXAMPLE 3 threo-2-(N-Benzyl-N-octylamino)-1-(6-methoxy-2-naphthyl)-propanol (MG 38077)

The compound of Example 2 (8.7 g) is hydrogenated at room temperature in methanol in the presence of Pd/C as the catalyst. After filtering off the catalyst the solution is evaporated to dryness under reduced pressure.

The residue is converted into the hydrochloride by the addition of hydrogen chloride in diethyl ether, then into the free base by conventional methods. Yield 4.2 g (61%); m.p. 102°–103° C.

| Analysis for $C_{22}H_{33}NO_2$% | calc. | C 76.92 | H 9.68 | N 4.08 |
|---|---|---|---|---|
| | found | 76.74 | 9.65 | 4.09 |

The NMR spectrum (CDCl$_3$) gave a value of J=8.4 Hz.

EXAMPLE 4 threo- and erythro-2-[4-(2-Oxo-1-benzimidazolinyl)-1-piperidinyl]-1-(6-methoxy-2-naphthyl)-propanol (MG 38065 and MG 38095)

A mixture of 14.84 g of 2-bromo-1-(6-methoxy-2-naphthyl)-1-propanone (50 mmole), 10 g of 4-(2-oxo-1-benzimidazolinyl)-piperidine (46 mmole), 4.25 g of NaHCO$_3$ (50 mmole) and 150 ml of methanol is refluxed with stirring for 4 hours. After cooling to room temperature, the precipitate is collected, washed with water and with diethyl ether and dried.

Yield 12.3 g (62.2%) of 2-[4-(2-Oxo-1-benzimidazolinyl)-1-piperidinyl]-1-(6-methoxy-2-naphthyl)-1-propanone (MG 38094), m.p. 216°–217° C.

The foregoing ketone (10 g, 23.3 mmole) is dissolved in 200 ml of methanol, then 1.76 g of NaBH$_4$ (46.5 mmole) dissolved in 10 ml of alkaline water is dropped into the solution heated to reflux. At the end of the addition heating is continued for additional 5 hours, then the mixture is cooled to room temperature and 100 ml of water are added.

The precipitate is collected and crystallized from chloroform/diethyl ether. The threo-isomer is thus obtained.

Yield 6.8 (68%) m.p. 254°–256° C. (dec.)

The filtrate is made acidic by the addition of aqueous 18% HCl and concentrated under reduced pressure. The residue is treated with ethyl acetate and made alkaline with aqueous 5% sodium carbonate. The organic layer is separated and evaporated to dryness under reduced pressure.

The residue is purified by flash chromatography through silica gel 60 Merck 230–400 mesh, using chloroform: methanol 95:5 then 90:10 as the eluent. After crystallization from methanol, 1.5 g of erythro isomer (yield 15%) are obtained, m.p. 178°–180.5° C.

The erythro isomer was also obtained in a 55% yield by hydrogenating the intermediate propanone, MG 38094 (see above), in the presence of PtO$_2$ in an acetic acid-methanol mixture art 55° under a pressure of 3 atm. After purification through silicagel using chloroform:methanol 95:5 as the eluent; the erythro form was substantially pure and free from traces of the threo isomer formed during the hydrogenation.

| Analysis for $C_{26}H_{29}N_3O_3$% | calc. | C 72.36 | H 6.77 | N 9.74 |
|---|---|---|---|---|
| threo-isomer | found | 72.21 | 6.76 | 9.72 |
| erythro-isomer | found | 72.19 | 6.75 | 9.73 |

The $^1$H NMR spectrum (300 MHz, CDCl$_3$) gave the following values:
threo-isomer:

delta$_H$: 9.77 (1H, brs, >N—H); 7.9–7.0 (10 H, m, 6H naphthalenic and 4 H)

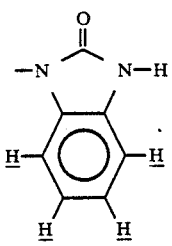

5.25 (1H, br, OH); 4.43 (1H, d,

J=9.8 Hz); 4.40 (1H, m, piperidinic); 3.93 (3H, s, OCH$_3$); 3.2–2.0 (7H, m, 6H piperidinic and 1H

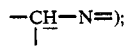

1.96 (2H, m, piperidinic); 0.84 (3H, d, —CH$_3$)
erythro-isomer
delta$_H$: 9.83 (1H, brs, >N—H); 7.9–7.0 (10H, m, 6H naphthalenic and 4H

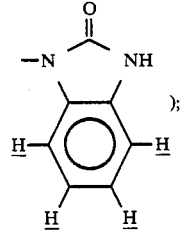

5.03 (1H, d

J=4.3 Hz); 4.36 (1H, m, piperidinic); 3.92 (3H, s, OCH$_3$); (1H, br, OH); 3.27 and 3.0 (2×1H, m, piperidinic); 2.91 (1H, m, =CH—N=); 2.7–2.2 (4H, m, piperidinic); 2.0–1.7 (2H, m, piperidinic); 0.97 (3H, d, —CH$_3$).

EXAMPLE 5 threo- and erythro-2-[4-(2-Furoyl)-1-piperazinyl]-1-(6-methoxy-2-naphthyl)-propanol (MG 38066 and MG 38078).

A mixture of 6.4 g of 2-bromo-1-(6-methoxy-2-naphthyl)-1-propanone (22 mmole), 3.6 g of 1-(2-furoyl)-piperazine (20 mmole) (Althuis et al., J. Med. Chem. 20, 146, 1977), 1.85 g of NaHCO$_3$ (22 mmole) and 50 ml of methanol is refluxed with stirring for 6 hours. After cooling to room temperature, 1.5 g of NaBH$_4$ (40 mmole) is gradually added, then stirring is continued for additional 3 hours.

The precipitate is collected and recrystallized from chloroform/ diethyl ether. Yield 2.2 g (27.9%) of threo isomer, m.p. 183°–184° C.

From the reaction mother liquor, by addition of 18% aqueous HCl, the erythro isomer precipitates out and is collected, converted into the free base and recrystallized from acetone/hexane.

Yield 3.7 g (46.9%); m.p. 126°–127° C.

| Analysis for $C_{23}H_{26}N_2O_4$% | calc. | C 70.03 | H 6.64 | N 7.10 |
|---|---|---|---|---|
| threo isomer | found | 69.82 | 6.62 | 7.08 |
| erythro isomer | found | 69.85 | 6.63 | 7.07 |

The NMR spectrum (CDCl₃) gave:
threo isomer J=9.8 Hz
erythro isomer J=4.0 Hz.

EXAMPLE 6 threo- and erythro-2-(4-Phenyl-1-piperazinyl)-1-(6-methoxy-2-naphthyl)-propanol (MG 38068 and MG 38088)

Prepared substantially by the process of Example 4, except that at the end of the hydrogenation the precipitate consisting of a mixture of the two diastereoisomers is separated by flash chromatography through Merck 60 silicagel 230–400 mesh, using first chloroform: acetone 95:5, then 80:20 as the eluent. After crystallization from chloroform/diethyl ether the yeilds are:
threo-isomer 2.3 g (50.1); m.p. 196°–198° C.
erythro-isomer 1.0 g (21.8%); m.p. 188°–189° C.

| Analysis for $C_{24}H_{28}N_2O_2$% | calc. | C 76.56 | H 7.49 | N 7.44 |
|---|---|---|---|---|
| threo isomer | found | 76.40 | 7.47 | 7.42 |
| erythro isomer | found | 76.42 | 7.47 | 7.43 |

The NMR spectrum (CDCl₃) gave:
threo-isomer J=9.5 Hz
erythro-isomer J=3.6 Hz.

EXAMPLE 7

2-[4-(2-Oxo-1-benzimidazolinyl)-1-piperidinyl]-1-(6-methoxy-2-naphthyl)-ethanol (MG 38069)

A mixture of 5.7 g of 2-bromoacetyl-6-methoxynaphthalene (20 mmole), 3.95 g of 4-(2-oxo-1-benzimidazolinyl)-piperidine (18 mmole); b 1.7 g of NaHCO₃ (20 mmole) and 60 ml of methanol is refluxed with stirring for 5 hours, then 1.4 g of NaBH₄ (37 mmole) dissolved in 7 ml of alkaline water is dropped while maintaining the reaction mixture at the boiling temperature.

Heating is continued for additional 12 hours, then the mixture is cooled and diluted with 60 ml of water. The precipitate s collected and crystallized from methanol/water. Yield 4.5 g (59.6%); m.p. 231°–233° C.

| Analysis for $C_{25}H_{27}N_3O_3$% | calc. | C 71.92 | H 6.52 | N 10.06 |
|---|---|---|---|---|
| | found | 71.77 | 6.50 | 10.04 |

¹H NMR (300 MHz CDCl₃) spectrum: delta_H: 9.79 (1H, br.s. >N—H); 8.0–7.0 (10H, m, 6H, naphthalenic and 4H

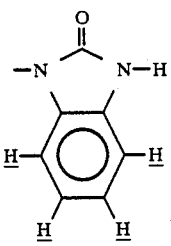

4.92 (1H, d.d.,

4.42 (1H, m,

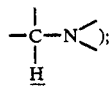

4.16 (1H, br, OH); 3.92 (3H, s, OCH₃); 3.42 (1H, m, piperidinic); 3.05 (1H, m, piperidinic); 2.75–2.60 (2H, m, —CH₂—N<); 2.60–2.30 (3H, m, piperidinic); 2.31 (1H, m, piperidinic); 2.1–1.8 (2H, m, piperidinic).

EXAMPLE 8-10

By substantially the same process as in the foregoing Example 4 and using NaBH₄ as the reducing agent the following compounds are prepared, with the properties and yields indicated.

2-[4-(1-Oxo-3-phenyl-2-propenyl)-1-piperazinyl]-1-(6-methoxy-2-naphthyl)-propanol.

threo isomer (MG 38071), yield 60.8%; m.p. 179°–181° C.; ¹H NMR
300 MHz CDCl₃) J=9.8 Hz
erythro isomer (MG 38079), yield 23.4%; m.p. 172°–174° C.; J=4.0 Hz 2-[4-(3-Pyridinecarbonyl)-1-piperazinyl]-1-(6-methoxy-2-naphthyl)-propanol
threo isomer (MG 38070), yield 34.2%, m.p. 182°–183° C.; ¹H NMR J=9.7 Hz
erythro isomer, (MG 38093) yield 26%, m.p. 160°–161° C.; J=4.0 Hz 2-[4-(1-Oxo-3-(3,4,5-trimethoxyphenyl)-2-propenyl)-1-piperazinyl]-1-(6-methoxy-2-naphthyl)-propanol
threo isomer (MG 28471), yield 33%, m.p. 162.5°–163.5° C.
erythro isomer (MG 28472), yield 24.1%, m.p. 165.5°–166.5° C.

The elemental analysis and the NMR spectra confirmed the structure of all the six above mentioned compounds.

EXAMPLE 11 threo- and erythro-2-[4-(2-Furoyl)-1-piperazinyl]-1-(6-methylthio-2-naphthyl)-propanol (MG 28446 and MG 28451)

To 50 g of 6-methylthio-2-naphthyl ethyl ketone (0.217 mole) (NG. Buu Hoi et al., J. Chem. Soc. 485, 1953) in 270 ml of anhydrous tetrahydrofuran, 81.61 g of phenyl trimethyl ammonium tribromide (0.217 mole)

are added at portions during 5 hours with stirring at room temperature.

The mixture is stirred overnight, then it is poured into ice water containing 10% of NaHCO3 and extracted with diethyl ether. The organic layer is washed with an aqueous 5% solution of Na2S2O3, dried over Na2SO4 and evaporated to dryness. The residue is recrystallized from isopropanol. Yield 62 g (92%) of 6-methylthio-2-naphthyl alpha-bromomethyl ketone, m.p. 118°–119° C.

A mixture of 22.65 g of the foregoing ketone (66.5 mmole), 12 g of 1-(2-furoyl)-piperazine (66.5 mmole), 6.15 g of NaHCO3 (73.2 mmole) and 120 ml of methanol is refluxed with stirring for one night. The mixture is then cooled and 5.03 g of NaBH4 (133 mmole) is gradually added at 0°–5° C. After one night at room temperature, to the mixture cooled at 0°–5° C. 100 ml of water is added and the precipitate is collected and purified by flash chromatography through silicagel Merck 60 230–400 mesh, with ethyl acetate: light petroleum 85:15 as the eluent.

Yield: threo-isomer 8.6 g (31.5%), m.p. 167°–168° C.; erythro-isomer: 8.9 g (32.6%), m.p. 144.5°–145.5° C.

| Analysis for C23H26N2O3S% | calc. | C 67.28 | H 6.38 | N 6.82 |
|---|---|---|---|---|
| threo-isomer, | found | 67.14 | 6.39 | 6.80 |
| erythro-isomer, | found | 67.18 | 6.37 | 6.80 |

The NMR spectrum gave J=9.7 Hz for the threo-isomer and J=3.7 Hz for the erythro-isomer.

EXAMPLE 12-18

Starting from 6-methyltio-2-naphthyl alpha-bromomethyl ketone (see Example 11) and reacting it with the appropriate amine by substantially the same process as the one used above for the preparation of the compound of Example 11, the following compounds are prepared, of which the yields and the melting points are reported. The elemental analysis and the NMR spectra confirmed the structure and the stereoisomeric form of all compounds.

EXAMPLE 12

2-[4-(1-Oxo-3,4,5-2-propenyl)-1-piperazinyl]-1-(6-methylthio-2-naphthyl)-propanol threo-isomer (MG 28447): 40.8%; m.p. 197.5°–199° C. J=9.7 Hz erythro-ixomer (MG 28452): 34.3%; m.p. 172°–172.5° C. J=3.7 Hz.

EXAMPLE 13

2-[4-(3-Pyridinylcarbonyl)-1-piperazinyl]-1-(6-methylthio-2-naphthyl)-propanol threo-isomer (MG 28453): 34.8%; m.p. 159°–160.5° C. J=9.5 Hz erythro-isomer (MG 28473): 25%; m.p. 110°–111° C. J=4 Hz

EXAMPLE 14 threo-2-(4-Phenyl-1-piperazinyl)-1-(6-methylthio-2-naphthyl)-propanol (MG 28428): 64%; m.p. 239.5°–240.5° C. J=9.9 Hz.

EXAMPLE 15 threo-2-[4-(2-Oxo-1-benzimidazonlinyl)-1-piperidinyl]-1-(6-methylthio-2-naphthyl)-propanol (MG 14167): 59.6%; m.p. 277°–278° C. J=9 Hz.

EXAMPLE 16

2-[4-(1-Oxo-3-(2-thienyl)-2-propenyl)-1-piperazinyl]-1-(6-methylthio-2-naphthyl)-propanol.

threo-isomer (MG 14168): 39%; m.p. 177.5°–178.5° C. J=9.8 Hz erythro-isomer (MG 14187): 24%; m.p. 153°–155° C. J=4 Hz

EXAMPLE 17 erythro-2-Octylamino-1-(6-methylthio-2-naphthyl)-propanol (MG 28280): 51%; m.p. 95°–95.5° C. J3.8 Hz

EXAMPLE 18

2-[4-(1-Oxo-3-phenyl-2-propenyl)-1-piperazinyl]-1-(6-methylthio-2-naphthyl)-propanol threo-isomer (MG 28295): 32.1%; m.p. 180°–181° C. J=8 Hz.

erythro-isomer (MG 28353): 25.4%; m.p. 158.5°–160° C. J=4 Hz.

EXAMPLE 19 threo-2-[4-(2-Methoxyphenyl)-1-piperazinyl]-1-(6-methoxy-2-naphthyl)-propanol (MG 38098).

Preparation according to Example 1 from the same bromoketone and 1-(2-methoxyphenyl)-piperazine through 2-[4-(2-methoxyphenyl)-1-piperazinyl]1-(6-naphthyl)-1-propanol (MG 38096); this intermediate has m.p. 106°–107° C., yield 85%.

Yield of the end compound 59%; m.p. 206°–208° C. J=9.5 Hz

EXAMPLE 20

2-(4-Benzamido-1-piperidinyl)-1-(6-methoxy-2-naphthyl)-propanol

Prepared according to Example 4 from the same propanone and 4-benzamidopiperidine. The intermediate amino ketone (MG 38141) has m.p. 175°–177° C. and is reduced using NaBH4 as the reducing agent.

threo-isomer (MG 38105): 26.6%; m.p. 237°–239° C. J=9.8 Hz erythro-isomer (MG 38127): 24.4%; m.p. 189°–191° C. J=4.0 Hz

EXAMPLE 21 threo-2-[4-(2-Oxo-1-benzimidazolinyl)-1-piperidinyl]-1-(6,7-dimethoxy-2-naphthyl)-propanol (MG 14233)

From 1-(6,7-dimethoxy-2-naphthyl)-1-propanone and phenyl trimethyl ammonium tribromide through 2-bromo-1-(6,7-dimethoxy-2-naphthyl)-1-propanone (yield 84%; m.p. 122°–124° C.) which is then reacted with 4-(2-oxo-1-benzimidazolinyl)-1-piperidine followed by reduction with LiAlH4. Yield 55%; m.p. 246°–248° C. J=9.5 Hz.

EXAMPLE 22

2-[4-(2-Oxo-1-benzimidazolinyl)-1-piperidinyl]-1-(6,7-dimethoxy-2-naphthyl)-ethanol (MG 14235)

From 1-(6,7-dimethoxy-2-naphthyl)-1-ethanone and phenyl trimethyl ammonium tribromide. The intermediate bromoketone (MG 14228; yield 65%; m.p. 136°–137.5° C.) is reacted with 4-(2-Oxo-1-benzimidazolinyl)-1-piperdine followed by reduction with LiAlH4 in tetrahydrofuran. Yield 60%; m.p. 205°14 207° C.

EXAMPLE 23 threo-2-[4-(2-Oxo-1-benzimidazolinyl)-1-piperidinyl]-1-(6-isopropoxy-2-naphtyl)-propanol (MG 14238)

6-Propionyl-2-naphthol and 2-iodopropane give 1-(6-isopropoxy-2-naphthyl)-1-propanone (m.p. 79°-80° C.) which is converted into the bromo derivative (MG 14226), m.p. 82°-83° C. This compound is processed as in the preceding Example. Yield 52%; m.p. 254°-256° C. J=9,8 Hz.

EXAMPLE 24

2-[4-(2-Oxo-1-benzimidazolinyl)-1-piperidinyl]-1-(6-isopropoxy-2-naphthyl)-ethanol (MG 14237)

Prepared as in Example 23 starting from 6-acetyl-2-naphthol through the corresponding ethanone (MG 14222 m.p. 54°-56° C.). The intermediate bromo ketone (MG 14224) has m.p. 91°-93° C. The end compound (MG 14237) has m.p. 217°-219° C.

EXAMPLE 25

2-[4-(2-Oxo-1-benzimidazolinyl)-1-piperidinyl]-1-(6-methoxy-2-naphthyl)-1-butanol From 2-bromo-1-(6-methoxy-2-naphthyl)-1-butanone and 4-(2-Oxo-1-benzimidazolinyl)-1-piperidine and reduction of the intermediate butanone (m.p. 177°-178° C.) with NaBH4. The steric isomers are separated as the hydrochlorides by crystallization from methanol.

threo-isomer (MG 14242): 60%; m.p. 218°-220° C. J=9.5 Hz erythro-isomer (MG 14247): 20%; m.p. 197°-198° C. J=4.7 Hz

EXAMPLE 26

2-[4-(2-Oxo-1-benzimidazolinyl)-1-piperidinyl]-1-(6-methoxy-2-naphthyl)-pentanol.

From 1-(6-methoxy-2-naphthyl)-1-pentanone through the 2-bromo derivative (m.p. 78°-80° C.) which is processed as in the foregoing Examples.

threo-isomer (MG 14250): 60%; m.p. 228°-230° C. (hydrochloride). J=9.5 Hz.

erythro-isomer (MG 14251): 15%; m.p. 140°-141° C. (hydrochloride). J=4.0 Hz.

EXAMPLE 27 threo-2-[4-(2-Oxo-5-chloro-1-benzimidazolinyl)-1-piperidinyl]-1-(6-methoxy-2-naphthyl)-propanol (MG 14239)

Prepared as in the preceding Example from 4-(2-oxo-5-chloro-1-benzimidazolinyl)-piperidine. Yield 60%; m.p. 274°-276° C. (dec.). J=9.8 Hz.

EXAMPLE 28

2-[4-(2-Methyl-1-benzimidazolinyl)-1-piperidinyl]-1-(6-methoxy-2-naphthyl)-propanol Prepared as in the preceding Example from 4-(2-methyl-1-benzimidazolinyl)-1-piperidine.

threo-isomer (MG 14249): 52%; m.p. 165°-167° C. J=9.6 Hz.

erythro-isomer (MG 14254): 20%; m.p. 159°-161° C. J=4Hz.

EXAMPLE 29

2-[4-(2-Oxo-1-benzimidazolinyl)-methyl-1-piperidinyl]-1-(6-methoxy-2-naphthyl)-propanol.

threo-isomer (MG 14263). 69%; m.p. 221°-223° C. J=9.5 Hz.

erythro-isomer (MG 14265). 15%; m.p. 177°-179° C. J=4.0 Hz.

EXAMPLE 30

2-[4-(2-Oxo-3-indolinylidene)-1-piperidinyl]0-1-(6-methoxy-2-naphthyl)-propanol threo-isomer (MG 14264): J=9.6 Hz.
erythro-isomer (MG 14266): J=4.0 Hz.

EXAMPLE 31

2-(1-Piperazinyl)-1-(6-methoxy-2-napthyl)-propanol

From 2-bromo-1-(6-methoxy-2-naphtyl)-1-propanone and 1-benzylpiperazine, the compound 2-(4-benzyl-1-piperazinyl)-1-(6-methoxy-2-naphtyl)-1-propanone is prepared (MG 14256; m.p. 89°-91° C., which is reduced with NaBH4 to the corresponding amino alcohol as a mixture of the two stereoisomeric forms which are separated by flash chromatography.

threo-isomer, (MG 14259), Yield 54%, m.p. 149°-150° C., J=9.8. Hz.

erythro-isomer, (MG 14260), Yield 24%, m.p. 172°-174° C., J=4 Hz.

There are debenzylated by hydrogenation in the presence of Pd/C as the catalyst.

threo-isomer (MG 14258), Yield 84%, m.p. 164°-166° C. J=10 Hz.

erythro-isomer, (MG 14262), Yield 63%, m.p. 208°-212° C., J=4 Hz.

We claim:

1. A compound of the formula:

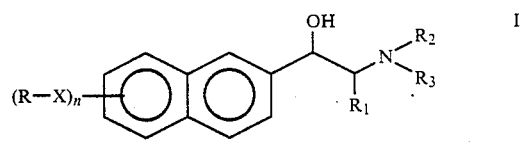

wherein R represents a lower straight or branched alkyl group, X represents —O— or —S—, n is an integer from 1 to 3, R1 represents hydrogen or a lower alkyl group; R2 represents hydrogen or benzyl; R3 represents an alkyl group; or alternatively R2 and R3 taken together represent a divalent group selected from:

(a)

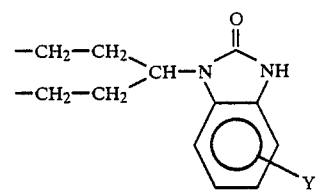

wherein Y represents hydrogen or halogen; and (b)

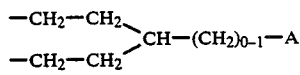

wherein A is a group selected from

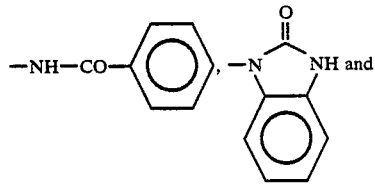

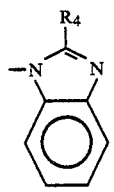

wherein R₄ represents a lower alkyl group and its salts with inorganic acids, organic acids, cationic exchange resins and complexes with cyclodextrins.

2. A compound selected from the stereoisomeric threo and erythro form of 2-[4-(2-oxo-1-benzimidazolinyl)-1-piperidinyl]-1-(6-methoxy-2-naphthyl)-propanol.

3. 2-[4-(2-Oxo-1-benzimidazolinyl)-1-piperidinyl]-1-(6-methoxy-2-naphthyl)ethanol.

4. A compound selected from the steroisomeric threo and erythro form of 2-(4-benzamido-1-piperidinyl)-1-(6-methoxy-2-naphthyl)-propanol.

5. A compound selected from the stereoisomeric threo and erythro form of 2-[4-(2-Oxo-1-benzimidazolinyl)-1-piperidinyl]-1-(6,7-dimethoxy-2-naphtyl)-propanol.

6. A compound of the formula:

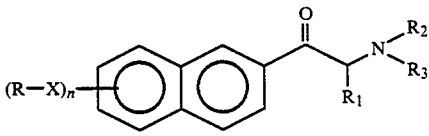

wherein R represents a lower straight or branched alkyl group, X represents —O— or —S—, n is an integer from 1 to 3, R₁ represents hydrogen or a lower alkyl group; R₂ represents hydrogen or benzyl; R₃ represents an alkyl group; or alternatively R₂ and R₃ taken together represents a divalent group selected from:

(a)

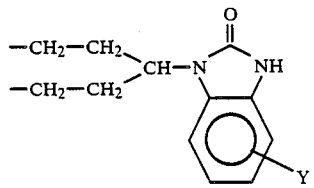

wherein Y represents hydrogen or halogen; and (b)

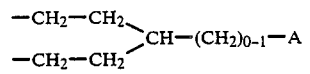

wherein A is is a group selected from

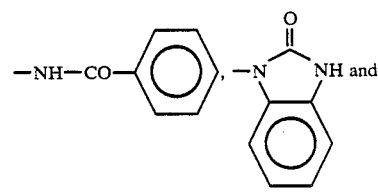

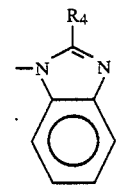

wherein R₄ represents a lower alkyl group.

* * * * *

UNITED STATES PATENT AND TRADEMARK OFFICE
CERTIFICATE OF CORRECTION

PATENT NO. : 4,902,799

DATED : FEBRUARY 20, 1990

INVENTOR(S) : GIAMPAOLO PICCIOLA ET AL.

It is certified that error appears in the above-identified patent and that said Letters Patent is hereby corrected as shown below:

Title page item [30], the Foreign Application Priority Data, delete "Oct. 14, 1985" and insert --Oct. 31, 1985--.

Signed and Sealed this

Twenty-fourth Day of September, 1991

*Attest:*

HARRY F. MANBECK. JR.

*Attesting Officer*   *Commissioner of Patents and Trademarks*